US 7,669,458 B2

(12) United States Patent
Commuri et al.

(10) Patent No.: US 7,669,458 B2
(45) Date of Patent: Mar. 2, 2010

(54) METHOD AND APPARATUS FOR PREDICTING DENSITY OF ASPHALT

(75) Inventors: Sesh Commuri, Norman, OK (US); Musharraf Zaman, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 282 days.

(21) Appl. No.: 11/271,575

(22) Filed: Nov. 10, 2005

(65) Prior Publication Data

US 2006/0096354 A1    May 11, 2006

Related U.S. Application Data

(60) Provisional application No. 60/626,596, filed on Nov. 10, 2004.

(51) Int. Cl.
*G01N 9/36* (2006.01)
*G01N 3/00* (2006.01)

(52) U.S. Cl. .......................... 73/32 A; 73/573
(58) Field of Classification Search ............... 73/32 A, 73/12.12, 594, 579, 573; 404/117, 75; 702/137
See application file for complete search history.

(56) References Cited

U.S. PATENT DOCUMENTS

| | | | |
|---|---|---|---|
| 3,998,090 A * | 12/1976 | Wislocki | .......... 73/12.12 |
| 4,103,554 A | 8/1978 | Thurner | |
| 5,402,667 A * | 4/1995 | Atkinson et al. | ......... 73/12.12 |
| 5,727,900 A * | 3/1998 | Sandstrom | .......... 404/84.1 |
| 6,122,601 A * | 9/2000 | Swanson et al. | ............ 702/137 |
| 6,431,790 B1 * | 8/2002 | Anderegg et al. | ............. 404/75 |
| 6,551,019 B1 * | 4/2003 | Motz et al. | ................... 404/117 |
| 6,577,141 B2 | 6/2003 | Gandrud | |
| 6,604,432 B1 * | 8/2003 | Hamblen et al. | .............. 73/784 |
| 6,786,077 B2 * | 9/2004 | Baumoel et al. | ............ 73/32 A |
| 6,829,986 B2 * | 12/2004 | Richter | ................... 100/155 R |
| 6,912,903 B2 * | 7/2005 | Hamblen et al. | .............. 73/573 |
| 6,941,793 B2 * | 9/2005 | Rioux | ....................... 73/12.11 |
| 7,216,543 B2 * | 5/2007 | Paik et al. | ..................... 73/579 |
| 2001/0037671 A1 * | 11/2001 | Bilmes et al. | ............... 73/32 A |
| 2002/0129653 A1 * | 9/2002 | Seth et al. | ..................... 73/594 |
| 2004/0035207 A1 * | 2/2004 | Hamblen et al. | ............. 73/573 |

OTHER PUBLICATIONS

Geodynamik Catalog ALFA-030, "Compactometer, compaction meter for vibratory rollers," entire catalog, undated but admitted to be prior art.

(Continued)

*Primary Examiner*—John Fitzgerald
(74) *Attorney, Agent, or Firm*—McAfee & Taft (57) ABSTRACT

A method and apparatus for predicting the quality of compaction of beds of material with a vibratory device as a function of the vibration of the compaction device, the material of the bed, the lift thickness, the temperature, among other process parameters is described in this invention. The vibration of the compacting device during the compaction of the bed is compared with the vibration characteristics of the compacting device on a bed of known properties. The quality of compaction of the bed is then estimated based on the knowledge of the process parameters. The output of the apparatus may be used as a visual input to the operator of the compacting device or stored in an electronic format to depict the progress during the compaction process.

25 Claims, 4 Drawing Sheets

OTHER PUBLICATIONS

Jean-Louis Briaud and Jeongbok Seo, "Intelligent Compaction: Overview and Research Needs," Report, Dec. 2003, Texas A&M University, entire document.

Edward J. Jaselskis, Hsiu Han, Lawrence Tan and Jonas Grigas, "Roller Mountable Asphalt Pavement Quality Indicator," 1998 Transportation Conference Proceedings, 1998, pp. 192-194.

Edward J. Jaselskis, Hsiu C. Han, Jonas Grigas, Lawrence Tan and Daniel Fahrion, "Status of Roller Mountable Microwave Asphalt Pavement Density Sensor," Journal of Construction Engineering and Management, pp. 46-52, Jan./Feb. 2001.

R. Edward Minchin, Jr. and H. Randolph Thomas, "Validation of Vibration-Based Onboard Asphalt Density Measuring System," Journal of Construction Engineering and Management, pp. 1-7, Jan./Feb. 2003.

Timothy R. Clyne, Xinjun Li, Mihai O. Marasteanu and Eugene L. Skok, "Dynamic and Resilient Modulus of Mn/DOT Asphalt Mixtures," Final Research Report, Feb. 2003, entire document, Minnesota Department of Transportation, Research Services, St. Paul, Minnesota.

Michael A. Mooney, Essam F. Tawfik, Godfrey B. Chan and Jie L. Pan, "Health monitoring during vibratory compaction of soil," Report, Apr. 8, 2003, entire document, School of Civil Engineering and Environmental Science and School of Electrical and Computer Engineering, The University of Oklahoma.

Ake J. Sandstrom and Carl B. Petterson, "Intelligent Systems for QA/QC in soil compaction," Report, Nov. 14, 2003, entire document, Geodynamik HT AB, Stockholm, Sweden.

Heinz F. Thurner and Ake Sandstrom, "Continuous Compaction Control, CCC," European Workshop Compaction of Soils and Granular Materials, Paris, May 19, 2000, pp. 237-246, Geodynamik AB, Stockholm, Sweden.

Tai-Sung Yoo and Ernest T. Selig, "Dynamics of Vibratory-Roller Compaction," Journal of the Geotechnical Engineering Division, Oct. 1979, pp. 1211-1231 and 1291-1295, vol. 105, No. GT10.

* cited by examiner

METHOD AND APPARATUS FOR PREDICTING DENSITY OF ASPHALT

CROSS REFERENCE TO RELATED APPLICATIONS

This application claims benefit of U.S. Provisional Application No. 60/626,596, filed Nov. 10, 2004, which is hereby incorporated herein by reference in its entirety.

BACKGROUND OF THE INVENTION

1. Field of Invention

The present invention relates generally to asphalt compaction, and more particularly, but not by way of limitation, to an improved method and apparatus for determining the degree of compaction of a bed of materials with a vibratory device.

2. Brief Description of Related Art

Asphalt is often used as pavement. In the asphalt paving process, various grades of aggregate are used. The aggregate is mixed with asphalt cement (tar), and a paver lays down the asphalt mix and levels the asphalt mix with a series of augers and scrapers. The material as laid is not dense enough due to air voids in the asphalt mix. Therefore, a roller makes a number of passes over the layer of asphalt material (mat), driving back and forth, or otherwise creating sufficient compaction to form asphalt of the strength needed for the road surface.

One of the key process parameters that is monitored during the compaction process is the compacted density of the asphalt mat. While there are many specifications and procedures to ensure that the desired density is achieved, most of these specifications require only one density reading per 1000 linear feet of the asphalt lane. The process of measuring density of the asphalt mat during the compaction process is cumbersome, time consuming, and is not indicative of the overall compaction achieved unless measurements are taken at a large number of points distributed in a grid fashion, which is difficult to achieve in the field due to cost considerations alone. Failure to meet the target density is unacceptable and remedial measures may result in significant cost overruns. Thus, there is a need to develop an intelligent monitoring system that will predict the compacted mat density in real-time, over the entire pavement surface being constructed. Because the density cannot be measured directly, researchers have attempted different methods for indirect measurements.

A method that has found some success involves the study of the dynamical characteristics of the vibratory compactors typically used in the field. The compactor and the asphalt mat can be viewed as a mechanically coupled system. An analytical model representing such a system can be used to predict the amount of compaction energy transferred to the mat as a function of frequency (coupled system). The amount of energy transferred can be viewed as a measure of the effectiveness of compaction. The machine parameters, like frequency and speed, can then be altered to maximize the energy transferred, thereby increasing the compaction. However, this method does not yield the compacted density directly; also, relating the energy dissipation to the compacted density is problematic. Therefore, this approach is not suitable to determine the level of compaction in an asphalt mat.

A number of researchers also tried to study the performance of the compactor during soil and asphalt compaction by observing the vibratory response of the compactor. The vibration energy imparted to the ground (sub-grade soil) during compaction also results in a vibratory response of the compactor. The amplitude and frequency of these vibrations are a function of the compactor parameters and the sub-grade. Thus, the observed vibrations of the compactor can be used to predict the properties of the material being compacted. U.S. Pat. No. 5,727,900 issued to Sandstrom discloses using the frequency and amplitude of vibration of the roller as it passes over the ground to compute the shear modulus and a "plastic" parameter of sub-grade soil. These values are then used to adjust the velocity of the compactor and its frequency and amplitude. Thus, this method attempts to control the frequency of the vibratory motors and the forward speed of the compactor for optimal compaction rather than estimate the density of the compacted soil.

Others methods involve estimating the degree of compaction by comparing the amplitude of the fundamental frequency of vibration of the compactor with the amplitudes of its harmonics. The compactor is instrumented with accelerometers to measure the vibrations of the compactor during operation. By relating the ratio of the second harmonic of the vibratory signal to the amplitude of the third harmonic, the compacted density is estimated with, in some cases, 80% accuracy. This means that the predicted density is within 1.5% of the actual density of the mat. These results are encouraging and validate the correlation between the observed vibrations and the property of the material being compacted. However, the accuracy of these techniques needs improvement, as the properties of the asphalt pavement are significantly different at 96.5% and 98% target densities. Further these methods are susceptible to variations in the data gathered.

Attempts have been made to account for some of the variations seen in the vibratory responses of compactors by considering the properties of the mix and the site characteristics, in addition to the vibratory response of the compactor, to estimate density. In one approach a microwave signal is transmitted through the asphalt layer, and the density is estimated based on the transmission characteristics of the wave. While the above techniques have been successful in demonstrating the feasibility of the respective approaches, they need to be further refined before they can be used to predict the density in the field with the required degree of precision.

SUMMARY OF THE INVENTION

The present invention is directed to a method and apparatus for determining the quality of compaction of a bed of material being compacted by a vibratory compactor. More specifically, the present invention enables the prediction of the density of an asphalt mat during the construction of an asphalt pavement.

In one aspect, the present invention is directed to a method for determining the density of a material by applying a vibratory energy to a first section of the material with a roller at a predetermined frequency and amplitude. The vibration characteristics of the roller are measured and a signal representing the vibratory characteristics of the roller is produced. The density of the first section of material is measured at selected locations, and the densities of the first section of material is correlated with the vibration signals to produce a density signal. Vibrations are then applied to a second section of material at a predetermined frequency and amplitude, and the vibratory characteristics of the roller relative to the second section of material is measured. A vibratory signal representing the vibratory characteristic of the roller is produced, and the vibratory signal of the roller of the second section of material is compared to the density signal of the first section of material to estimate the compaction of the second section of material.

In another aspect, the present invention is directed to a method for determining the density of an asphalt mat by comparing a vibratory signal derived from a roller rolling the asphalt mat with a predetermined density signal to estimate the compaction of the asphalt mat.

In yet another aspect, the present invention is directed to an asphalt compaction analyzer system for a roller. The asphalt compaction analyzer system includes at least one sensor mountable on the roller for producing signals indicative of a dynamic property of an asphalt mat as the roller rolls the asphalt mat; and means for estimating the compaction of the asphalt mat in real time based on the signals produced by the at least one sensor.

DETAILED DESCRIPTION OF THE INVENTION

Figure 1:
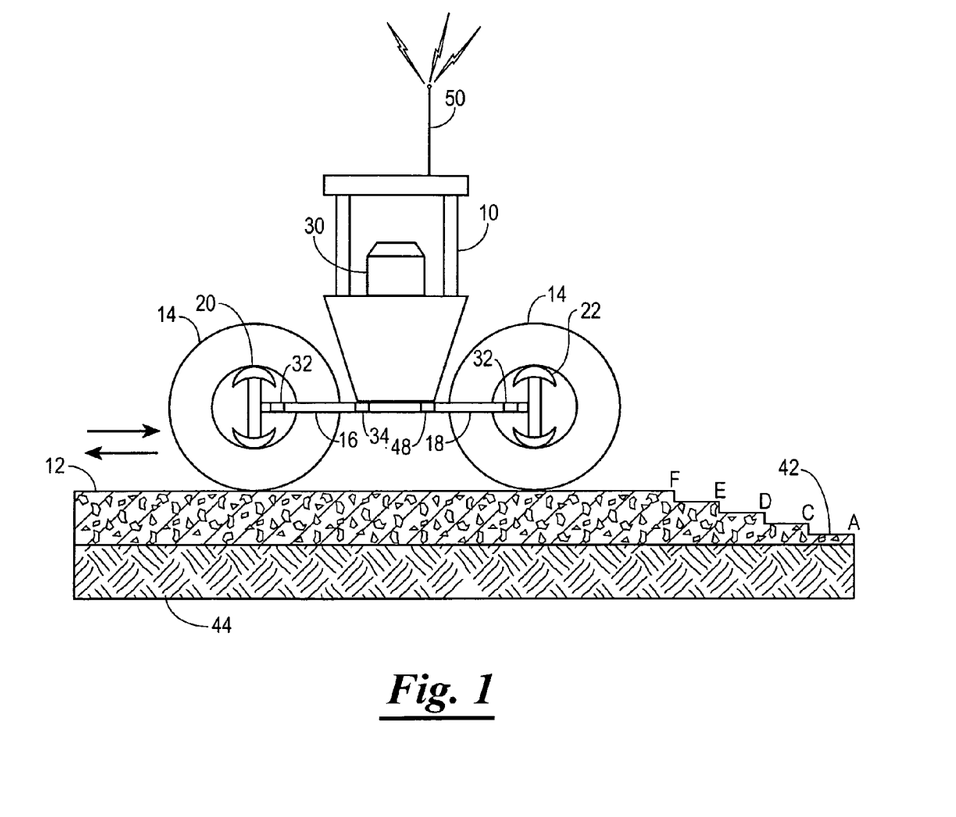
FIG. 1 is a schematic illustration of a vibratory roller provided with an asphalt compaction analyzer system constructed in accordance with the present invention.

Referring now to FIG. 1, a schematic illustration of a vibratory roller 10 commonly used in the field to compact an asphalt mat 12 is shown. The vibratory roller 10 includes two steel drums 14 that are mounted on axles 16 and 18 to which eccentric weights 20 and 22 are attached. The weights are rotated by means of vibration motors (not shown). The rotation of the eccentric weights 20 and 22 within the drums 14 causes an impact force at the contact between the drums 14 and the asphalt mat 12. The amplitude of these impacts is a function of the displacement of the eccentric weights 20 and 22. The spacing between subsequent impacts on the asphalt mat 12 is a function of the speed of rotation of the eccentric weights 20 and 22 and the forward speed of the roller 10. Thus, for a specified roller 10, the amount of compaction achieved or the density achieved is a function of the frequency and amplitude of the vibrations.

The vibratory roller 10 is provided with an asphalt compaction analyzer system 30, for predicting the density of an asphalt mat constructed in accordance with the present invention. The asphalt compaction analyzer system 30 receives input signals from vibration or movement sensors, such as accelerometers 32 which are connected to the axles 16 and 18 of the vibratory roller 10. The sensors generate a signal representing the acceleration of the axles to which the rollers 10 are connected, in a vertical and horizontal direction, respectively.

The vibratory response of the roller 10 is the primary parameter analyzed to determine the amount of compaction achieved. However, other parameters may affect compaction, such as temperature of the mat 12. To this end, a temperature sensor, such as infrared sensor 34 may also be mounted on the roller 10 to monitor the temperature of the mat 12. Other parameters affecting compaction are lift thickness, mix type, and type of roller used. However, these parameters need not be monitored during the process as they are static and can be taken into consideration during analyses.

Figure 2:
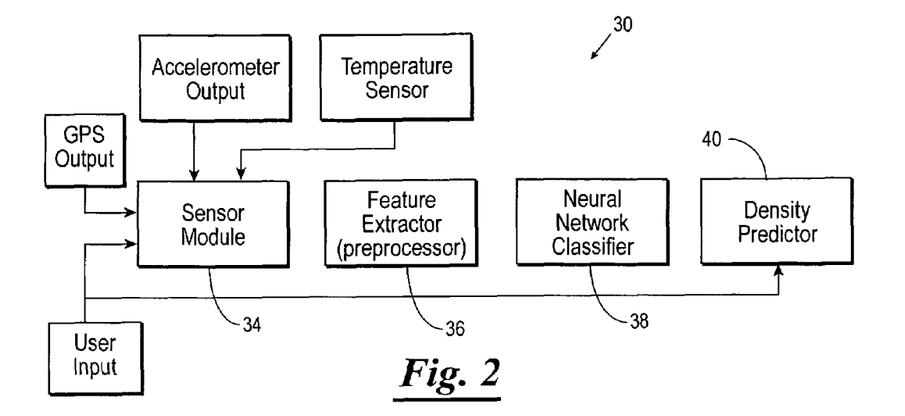
FIG. 2 is a schematic representation of the asphalt compaction analyzer system.

Referring now to FIG. 2, the operation of the asphalt compaction analyzer system 30 is based on the hypothesis that the features extracted from the vibration signal of the roller 10 are the primary source to determine the density in real time. The asphalt compaction analyzer system 30 comprises a sensor module 34, a feature extraction module 36, a neural network classifier 38, and a density predictor 40.

Target density is specified as a percentage of the density achieved on a control strip. That is, a control strip asphalt mat 42 is first laid on a sub grade 44 and compacted as shown in FIG. 1. On the control strip asphalt mat 42 the vibratory roller 10 is operated in one direction during a first pass (represented by AC in FIG. 1) and data from the sensors is collected and stored. Then the roller 10 is moved in an opposite direction and again a set of data is collected for a second pass (represented by CD in FIG. 1). As shown in the FIG. 1, the control strip asphalt mat 42 under controlled set of conditions is compacted for a plurality of different passes. For example, the control strip asphalt mat 42 may be compacted for several passes. After compaction, the density measures on the different thickness strips are obtained using conventional equipment and techniques, such as using a nuclear density gauge and also obtaining core samples to measure density in the laboratory. The data or the signals obtained during compaction on the control strip asphalt mat 42 are processed and used as a reference to predict the density during compaction in the field.

Referring again to FIG. 2, the sensor module 34 receives signals from the sensors, such as the accelerometers, temperature sensors, GPS sensor, and user input data, and processes or filters such signals to eliminate noise and other undesirable quantities. Low pass and band pass filters may be used to isolate frequency of interest in the signal. The output from the sensor module 34 is fed to the feature extraction module 36. The extraction module 36 extracts those frequency components of the signal that are indicative of the level of compaction. Typically, but not by way of limitation, these are the fundamental frequency of vibration and its harmonics. It is noted that there are a number of parameters like the mix type, mix temperature, sub-grade characteristics, and type of roller that influence the density, and thereby the properties, of the finished pavement. These parameters can be considered to be of two types: static parameters and dynamic parameters. Static parameters are those parameters that are known and do not change over the duration of the construction of the asphalt pavement. Typical static parameters are the aggregate size, gradation, number of fractured faces, type of asphalt binder and quantity used, the type of roller used for compacting the asphalt mat, and number of rollers. Because these parameters are known they do not need to be sensed. The dynamic parameters are those process parameters that change over the duration of the construction of the pavement. These include the environmental parameters (ground temperature, air temperature, wind speed), material parameters (temperature of the hot mix asphalt, lay down temperature, lift thickness), process parameters (speed of the roller, frequency of vibratory motors, number of passes), and machine parameters (vibration of the machine).

The vibration signals sensed by the accelerometers 32 will be used to determine the number of spectral components (frequencies and their amplitudes) needed to determine the salient features of the vibration signal. This is done using a computationally efficient algorithm, such as a Fast Fourier Transform (FFT). However, narrow band, band pass filters may also be used. Data collected from the accelerometers 32 operating in a controlled field environment will be used to design the FFT algorithm of the feature extractor module 36.

The accelerometers 32 mounted on the axles 16 and 18 of the roller 10 will provide the data input to the feature extraction module 36. A spectrogram of the input signal will be analyzed to verify if the frequency content and trends match with those seen in laboratory testing. By comparing the spectrogram of the signal with a known spectrum obtained during laboratory testing, the feature extraction module 36 will be reconfigured to include more spectral components if there exist any discrepancy in the signals compared. If discrepancies exist, then the feature extractor module 36 will be modified to include more spectral components to adequately represent the essential features.

To predict the density of the asphalt mat 12 in real-time from the vibratory signals obtained from the roller 10, the relationship between the various process parameters like mix type, sub-grade characteristics, mat temperature, and type of roller is modeled. This is accomplished using a number of techniques borrowed from the digital signal processing field, primarily in the area of pattern recognition and classification. Traditionally, this involved constructing a multi-dimensional map relating the accelerometer readings and the process parameters to the density or level of compaction of the asphalt mat 12. Once this map is developed, then given the accelerometer 32 reading during compaction and the knowledge of the process parameters, the density can be computed by a "look-up table" of the multi-dimensional map. However, the development of such a map is difficult in practice. Ignoring some of the process parameters in the model will lead to partial solutions or solutions that are not accurate.

In the present invention, the accelerometers 32 outputs are obtained when compacting the test strip to a specified density. Thereafter, the accelerometer 32 readings during compaction are compared to the known signal to estimate the amount of compaction achieved. Therefore, it is necessary to have an adaptive pattern recognition system that can first "learn" the desired signal characteristics before it can "classify" the vibratory signals. The adaptive pattern recognition system can be implemented, for example, by means of the neural network classifier 38, or alternatively, by fuzzy logic classifier or numerical technologies. The features extracted from the accelerometer 32 output can be classified into different classes representative of the amount of compaction achieved. A brief background on the neural network technique and its application in classification pertaining to the present invention.

Figure 3:
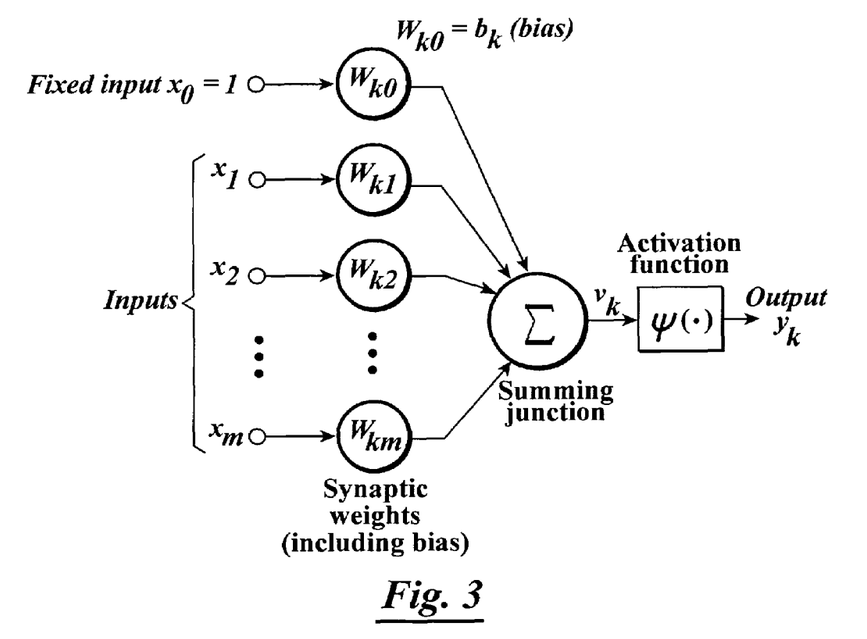
FIG. 3 is a graphical representation of a neuron.
Figure 4A:
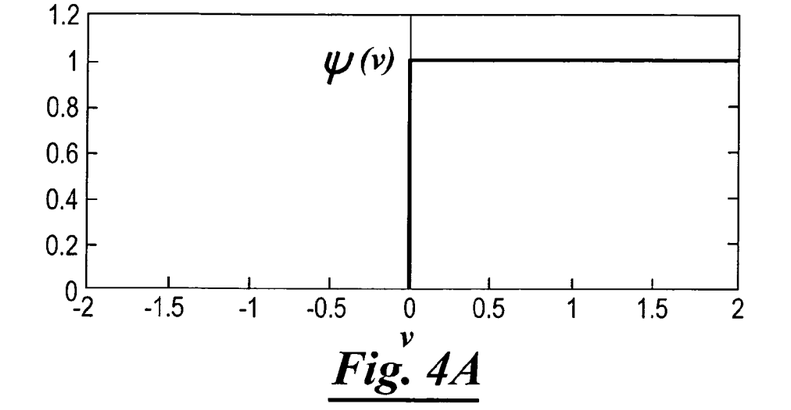
FIG. 4 is a graphical representation of activation functions of a neuron.
Figure 4B:
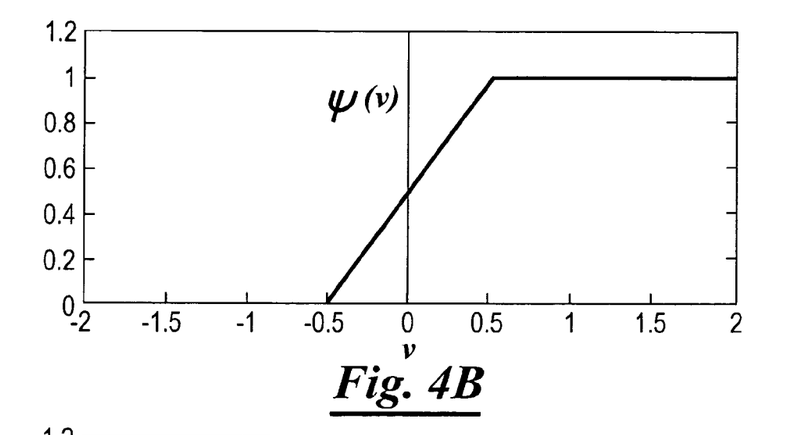
Figure 4C:
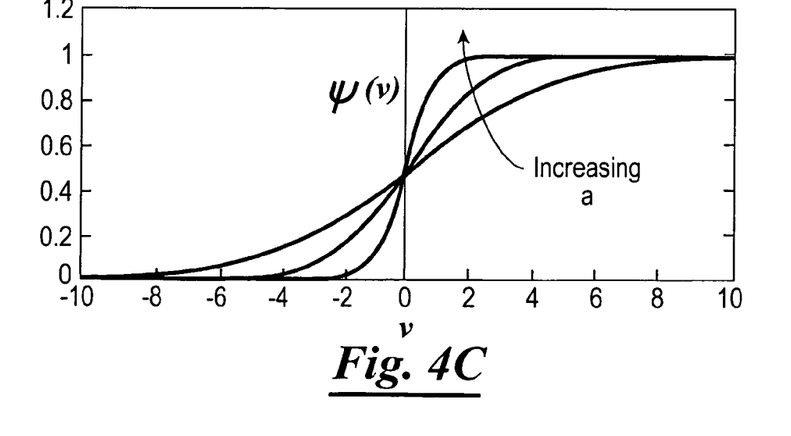
Figure 5:
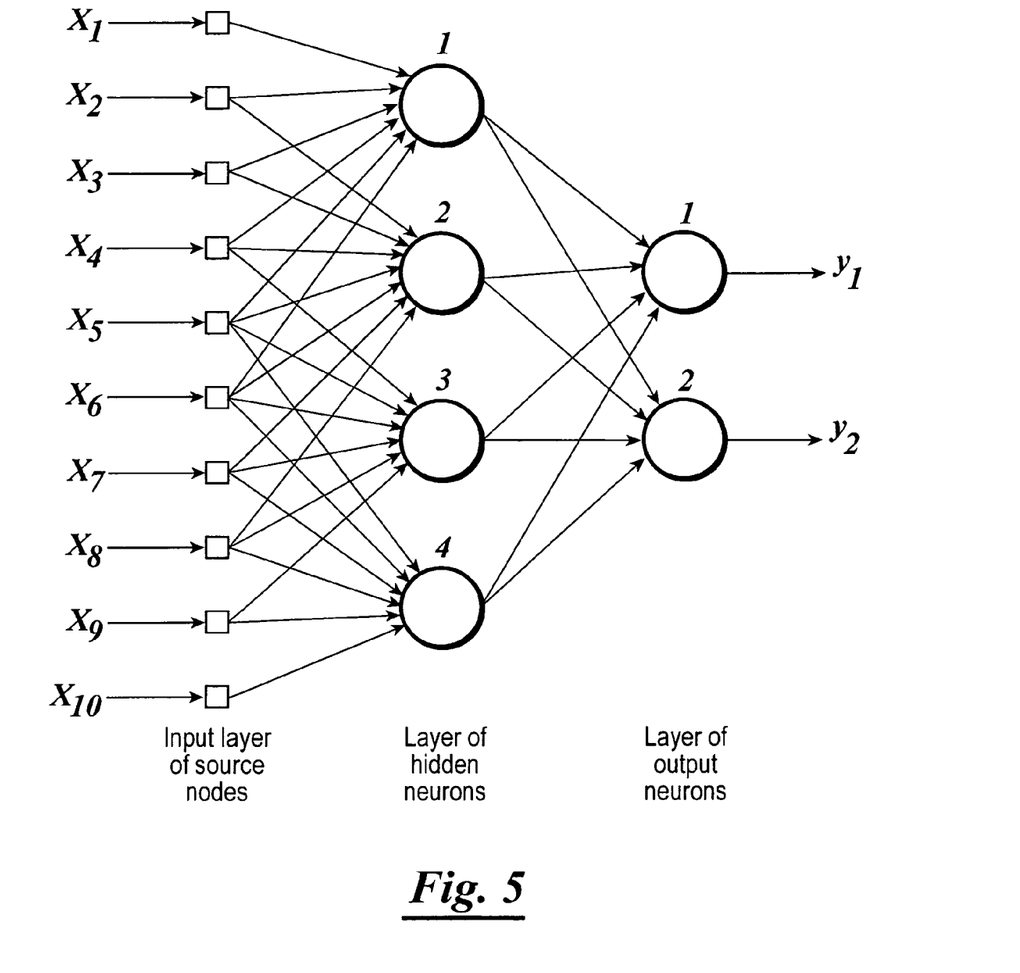
FIG. 5 is a schematic representation of four neurons in the hidden layer and two neurons in the output layer.

An artificial neural network is an interconnection of information processing elements called neurons. The block diagram of a typical neuron is shown in FIG. 3. The neuron includes three main elements: (i) a set of connecting links, called synapses characterized by a weight, (ii) an adder for summing up the input signals weighted by the respective synapses, and (iii) an activation function for limiting the output of the neuron. Typical activation functions for the neurons are shown in FIG. 4A-4C. More specifically, FIG. 4A shows a threshold function, FIG. 4B shows a piecewise linear function, and FIG. 4C shows a Sigmold function for varying slope parameter a. A multi-layer neural network 38 can be constructed using these computational elements as shown in FIG. 5. Networks like this have been successfully applied to the classification of objects from the spectral characteristics of their radar images. Neural networks have a natural ability for pattern classification. To exploit this property, the network is trained using standard back-propagation methods by presenting it with the features extracted from the accelerometer 32 outputs, as discussed below.

The features extracted from the accelerometer 32 outputs form the input to the neural network classifier 38. The number of input nodes of the neural network classifier 38 are selected based on the number of features that are extracted. The number of output nodes depend on the resolution of the classification that is desired. In order to train the neural network 38, the data sets for the training must first be collected. This can be done in the field by adopting a rolling plan as shown in FIG. 1. More specifically, after each pass of the roller, the starting point is staggered so that the section AC reflects the property of the asphalt mat after one pass of the roller 10. Similarly, the section CD represents the property of the asphalt after a second pass. Typically, four to five passes of compaction are carried out. Once the process of compaction is complete, core from the sections AC, CD, DE, and EF are extracted after the asphalt mat has cooled and the density of the cores are measured using conventional methods.

The density information is used to calibrate the nuclear density readings and will also serve as the training data for the neural network 38. The neural network 38 is trained using the vibratory signals collected and the density information until it can correctly classify the signals.

Based on the signals collected during different passes and the features extracted a multi layer neural network 38 is trained to classify the incoming signals. Training of the neural network 38 in the simplest way can be thought of as assigning a particular density value that is obtained by two different measures on the control strip to the signal related to that particular pass. Thus, whenever neural network 38 is given an input signal that has the features for example corresponding to the signal obtained from pass 2 then the network classifies the signal and assigns a particular class which in turn is the density value corresponding to the second pass.

Once the neural network classifier 38 is trained, the network automatically classifies the features extracted from the accelerometer 32 outputs into classes representative of the density. At this stage, it is assumed that the sub-grade 44 and machine characteristics do not alter over the entire length of the pavement. Thus, the classification of the extracted features is indicative of the properties of the asphalt mat 12. The output of the neural network 38 is then used by the density predictor 40 to predict the density of the asphalt mat 12 during compaction.

The density predictor 40 is configured to present the output of the neural network 38 in a user friendly manner, such as an audio and/or visual signal. For example, the density predictor 40 could indicate if the density of the asphalt mat 12 is equal to that of the asphalt control strip 42 with a visual signal. The density predictor 40 can also read in the process information, such as the mat temperature and the GPS input, to provide the user maps of the density or the temperature of the mat versus the position of the roller 10, for each roller pass. The density predictor 40 may also be configured to factor in the mat temperature, lift thickness, and vehicle speed, and predict the density of the mat based on the classification of the acceleration signal. This would then enable one to account for variations in the process parameters and predict changes in the sub-grade characteristics.

Thus, the density predictor 40 takes the signals from the sensors as input and displays the percentage density achieved as output. Output can be displayed as a set of colored lights on a display panel such that each color corresponds to a particular percentage or a range of density achieved. A second method of observing the output is a continuous signal that relates the position of the roller 10 versus percentage density achieved. To obtain the second method of display GPS sensors 48 and antenna 50 (FIG. 1) are mounted on the roller 10 to obtain the position of the roller 10.

From the above description, it is clear that the present invention is well adapted to carry out the objects and to attain the advantages mentioned herein, as well as those inherent in the invention. While a presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. A method for determining the density of a material, comprising:
  moving a roller along a first section of material;
  applying with the roller a vibratory energy at a predetermined frequency and amplitude to the first section of the material as the roller moves therealong;
  measuring the vibratory characteristics of the roller on the first section of material;
  producing a first section vibration signal representing the vibratory characteristics of the roller on the first section of material;
  measuring the density of the first section of material;
  correlating the density of the first section of material and the first section vibration signal;
  moving the roller along a second section of material;
  applying with the roller a vibratory energy at a predetermined frequency and amplitude to the second section of material as the roller moves therealong;
  measuring the vibratory characteristics of the roller on the second section of material;
  producing a second section vibration signal representing the vibratory characteristics of the roller on the second section of material; and
  comparing the second section vibratory signal to the first section vibratory signal to estimate the density of the second section of material.

2. The method of claim 1 wherein:
  the vibratory characteristics of the roller on the first section of material comprise amplitudes at a plurality of frequencies; and
  the vibratory characteristics of the roller on the second section of material comprise amplitudes at the plurality of frequencies.

3. The method of claim 1, further comprising generating a readable output signal to reflect that the second section vibratory signal is similar to the first section vibratory signal thereby indicating that the density of the second section material is at a desired density.

4. The method of claim 1 wherein the vibratory characteristics of the roller are frequencies and corresponding amplitudes.

5. The method of claim 1, further comprising:
  measuring the vibratory characteristics of the roller on the first section of material at a plurality of selected locations on the first section of material;
  providing a plurality of first section vibration signals representing the vibratory characteristics of the roller at the plurality of selected locations;
  measuring densities of the first section at a plurality of selected locations; and
  correlating the measured densities of the first section of material with the first section vibration signals wherein the comparing step comprises comparing the second section vibration signal to the plurality of first section vibration signals.

6. The method of claim 5 further comprising:
  continuously measuring the vibratory characteristics of the roller on the second section of material as the roller moves therealong; and
  producing a plurality of second section vibration signals representing the vibratory characteristics of the roller on the second section of material at different times as the roller moves along the second section of material, the comparison step comprising comparing the plurality of second section vibration signals with the plurality of first section vibration signals.

7. The method of claim 1, the moving step on the first section of material comprising:
  making a plurality of passes on the first section of material;
  the measuring vibratory characteristics step on the first section comprising measuring the vibratory characteristics of the roller on the first section of material at selected locations after each pass of the roller;
  the producing step on the first section of material comprising producing a plurality of first section vibration signals representing the vibratory characteristics at the selected locations;
  the measuring the density of the first section of material comprising measuring the density of the first section at a plurality of selected locations corresponding to the selected locations at which vibratory characteristics are measured; and
  correlating the measured densities of the first section of material with the first section vibration signals.

8. The method of claim 7, wherein one of the measured densities comprises a predetermined desired density, and wherein the roller is moved along the second section of material until the second section vibration signal is substantially the same as the first section vibration signal that correlates to the predetermined desired density.

9. A method for estimating the density of an asphalt mat, comprising the steps of:
  dividing an asphalt control strip into control strip portions;
  making a plurality of passes over the asphalt control strip with a roller, each control strip portion receiving a different number of passes;
  producing control strip vibratory signals indicative of the vibration characteristics of the roller for each of the control strip portions;
  measuring the density of the control strip on the control strip portions to generate a plurality of known measured densities;
  correlating the vibration signal of each control strip portion with the known measured density of the control strip portion;
  identifying the known measured density that represents a desired density for the asphalt mat and identifying the control strip vibratory signal that correlates thereto;
  rolling the asphalt mat with the roller; and
  comparing a vibratory signal derived from the roller rolling the asphalt mat with the control strip vibratory signals that correlate with the known measured densities to estimate the density of the asphalt mat, the vibratory signal of the roller rolling the asphalt mat being characterized by selected vibration characteristics of the roller.

10. The method of claim 9 further comprising ceasing rolling the asphalt mat when the vibratory signal derived during rolling the asphalt mat is such that the density of the asphalt mat is estimated to be the desired density.

11. The method of claim 9 wherein the vibration characteristics comprise selected frequencies and amplitudes at the selected frequencies.

12. The method of claim 9, the selected vibration characteristics comprising selected frequencies and amplitudes of the selected frequencies.

13. An asphalt compaction roller, comprising:
- at least one drum for rolling upon and compacting an asphalt mat;
- means for impacting the at least one drum to cause an impact force at the contact between the at least one drum and the asphalt mat;
- at least one sensor for measuring a vibratory response of the roller to the impact force; and
- comparison means for comparing vibration signals indicative of the vibratory response of the roller on the asphalt mat with previously collected signals indicative of a vibratory response of the roller on an asphalt control strip having the same or similar characteristics of the asphalt mat.

14. The asphalt compaction roller apparatus of claim 13 further comprising storage means for storing the previously collected vibratory signals.

15. The asphalt compaction roller apparatus of claim 13 wherein the means for impacting comprises an eccentric weight rotatable relative to the at least one drum.

16. The asphalt compaction roller apparatus of claim 13 further comprising a display mounted to the roller for displaying a readout indicating that the vibratory response of the roller on the asphalt mat is such that a desired density of the asphalt mat has been achieved.

17. The asphalt compaction roller apparatus of claim 16, wherein at least one of the previously collected vibratory signals correlates to a desired density on the control strip, the apparatus further comprising a display for displaying a readout to indicate when the vibratory signal of the roller on the asphalt mat is about the same as the vibratory signal that corresponds to the desired density achieved on the control strip.

18. Method for compacting an asphalt mat with a roller to a desired density comprising:
- making a plurality of passes on a control strip with the roller;
- applying a vibratory energy to the control strip with the roller during each pass;
- sensing the vibratory responses of the roller to the applied vibratory energy;
- determining the density of the control strip at selected locations;
- generating control strip vibratory signals representative of the vibratory responses of the roller to the applied vibratory energy during at least some of the passes over the control strip;
- correlating the control strip vibratory signals to the determined densities, one of the determined densities comprising a predetermined desired density;
- moving the roller along a first length of the asphalt mat to be compacted;
- generating asphalt mat vibratory signals representative of vibratory responses of the roller to applied vibratory energy as the roller moves along the first length of the asphalt mat; and
- comparing the asphalt mat vibratory signals with the control strip vibratory signals.

19. The method of claim 18, the determining step comprising obtaining core samples from the control strip and measuring the density of the core samples.

20. The method of claim 18 wherein the control strip is divided into control strip portions, the control strip portions receiving different numbers of passes, and wherein the determined density for each control strip portion is correlated with the vibratory signal generated for that control strip portion.

21. The method of claim 18, the applying step comprising impacting the roller where the roller comes into contact with the control strip at spaced time intervals.

22. The method of claim 18, further comprising:
- ceasing the moving step when asphalt mat vibratory signal on the first length of the asphalt mat being compacted is similar to the vibratory signal that correlates to the predetermined desired density such that the density of the first length is estimated to be within a desired range of the predetermined desired density; and
- repeating the moving, generating asphalt mat vibratory signals, and comparing steps for at least one other length of the asphalt mat to be compacted.

23. The method of claim 18, wherein the step of generating asphalt mat vibratory signals comprises:
- impacting the roller where the roller comes into contact with the asphalt mat at spaced intervals;
- measuring the vibratory responses to the impacting step of the roller moving along the asphalt mat; and
- generating asphalt mat vibratory signals representative of the vibratory responses.

24. The method of claim 23 further comprising stopping the moving step when the asphalt mat vibratory signal is similar to the control strip vibratory signal representative of the predetermined density to reflect that the asphalt mat is at, or within an acceptable deviation from the predetermined desired density.

25. The method of claim 24 further comprising repeating the moving, generating and comparing steps for at least one other length of the asphalt mat.

* * * * *